United States Patent
Falkvall et al.

[11] Patent Number: 6,143,181
[45] Date of Patent: Nov. 7, 2000

[54] DIALYSIS MACHINE WITH CONTROL PANEL

[75] Inventors: Thore Falkvall, Helsingborg; Per-Olov Carlsson, Ronneby; Lars-Olof Sandberg, Ronneby; Bjorn Gillerfalk, Ronneby, all of Sweden

[73] Assignee: Althin Medical AB, Ronneby, Sweden

[21] Appl. No.: 09/117,887

[22] PCT Filed: Jun. 13, 1997

[86] PCT No.: PCT/SE97/01050

§ 371 Date: Sep. 29, 1998

§ 102(e) Date: Sep. 29, 1998

[87] PCT Pub. No.: WO97/47336

PCT Pub. Date: Dec. 18, 1997

[30] Foreign Application Priority Data

Jun. 13, 1996 [SE] Sweden .................................. 9602330

[51] Int. Cl.⁷ .................................................. B01D 61/32
[52] U.S. Cl. ...................... 210/646; 210/143; 604/4.01; 361/681; 345/173; 248/918
[58] Field of Search ............................... 210/85, 86, 143, 210/257.1, 541, 542, 646, 647, 739; 345/173; 604/4–6, 4.01, 5.01, 6.01, 6.09; 361/680, 681, 682; 348/917, 918, 919

[56] References Cited

U.S. PATENT DOCUMENTS

| 5,487,827 | 1/1996 | Peterson et al. | 210/87 |
| 5,674,404 | 10/1997 | Kenley et al. | 210/646 |
| 5,679,245 | 10/1997 | Manica | 210/646 |
| 5,770,064 | 6/1998 | Jonsson et al. | 210/646 |
| 5,788,851 | 8/1998 | Kenley et al. | 210/646 |
| 5,824,213 | 10/1998 | Utterberg | 210/646 |
| 5,858,239 | 1/1999 | Kenley et al. | 210/646 |
| 5,895,571 | 4/1999 | Utterberg | 210/646 |

FOREIGN PATENT DOCUMENTS 0 505 037 A1  9/1992  European Pat. Off. .
WO 96/24396   8/1996  WIPO .

*Primary Examiner*—Joseph W. Drodge
*Attorney, Agent, or Firm*—Paula J. Kelly; Charles R. Mattenson; Robert M. Barrett

[57] ABSTRACT

Dialysis machine for alternatively hospital care and self-care having a touch screen (16) which can be adjusted universally and to a desired vertical position on the dialysis machine and can be locked in the desired adjusted position. As a consequence thereof, the touch screen can be arrested in a position in relation to the position of the person controlling the dialysis machine which allows the touch screen to be comfortably reached irrespective of the position of said person.

21 Claims, 5 Drawing Sheets

DIALYSIS MACHINE WITH CONTROL PANEL

This application is a 371 application of International Patent Application PCT/SE97/01050, filed on Jun. 13, 1997.

BACKGROUND OF THE INVENTION

The invention relates to a dialysis machine with a control panel comprising a touch screen.

In prior art dialysis machines having a touch screen this is mounted in a fixed position on the dialysis machine on the front side of the machine and at the top thereof where the screen can be easily reached by a nurse or another person responsible for the dialysis treatment, who is standing on the floor in front of the machine.

The cost increase in the dialysis care due to the continuously increasing number of patients—the increase is at present about 9% per year—enforces an increasing need of so called self-care at home or at some other place outside the hospitals, which means that it is the patient himself who controls the dialysis machine during the dialysis treatment the total care expense being lower as a consequence thereof. The touch screen is ideal for self-care because it requires no pressure forces at the control, only a touch of the screen at the intended position being sufficient, and because the information on the screen can be very easily understood by the patient also in a critical situation. On a touch screen symbols and fields which function as control buttons, and also indications can be designed such that only those as are relevant to the actual treatment situation are shown. As a consequence thereof the patient has no possibility to wongly engage into the treatment procedure as is the case when only "real" buttons are provided for the control. Since the patient is sitting or laying during the dialysis treatment the touch screen of prior art dialysis machines cannot be reached by the patient as easily as by a nurse who is standing in front of the machine. Some effort has to be exercised by the patient in order to reach the touch screen and to read the same and to effect the touches of the fields or symbols shown on the touch screen as required in order to adjust the dialysis machine in one respect or the other during the progress of the dialysis treatment. It is necessary that the control can be effected by one hand only—the left or the right hand—since the other hand or arm is connected to the machine by means of blood hoses during the dialysis treatment, and that the control can take place without effort considering the fact that dialysis patients often are very weak.

The proportion of the treatment which takes place as self-care is, however, still so small that it is not possible to develop dialysis machines intended particularly for this type of treatment.

SUMMARY OF THE INVENTION

In order that the touch screen can be easily reached by the patient irrespective of the patient being in a sitting or laying position, with due consideration of the circumstances and requirements mentioned above and without impairing the availability for the person standing on the floor in front of the dialysis machine, so that the dialysis machine is well suited for hospital care as well as self-care the dialysis machine according to the invention has obtained the features as claimed herein.

Although EP-A1-0 505 037 describes an anesthesia machine having a screen which can be adjusted by means of a handle about the horizontal axis and a vertical axis to be placed in a desired position and a desired orientation. In this case the screen cannot, however, be adjusted vertically and there are no means for arresting the screen in the desired adjusted position. It must be held manually in this position. The screen is no touch screen the control of the machine being effected by means of control elements on the handle.

BRIEF DESCRIPTION OF THE DRAWINGS

In order to explain the invention in more detail an illustrative embodiment thereof will be described below reference being made to the accompanying drawings in which.

DETAILED DESCRIPTION OF THE PRESENTLY PREFERRED EMBODIMENTS

Figure 1:
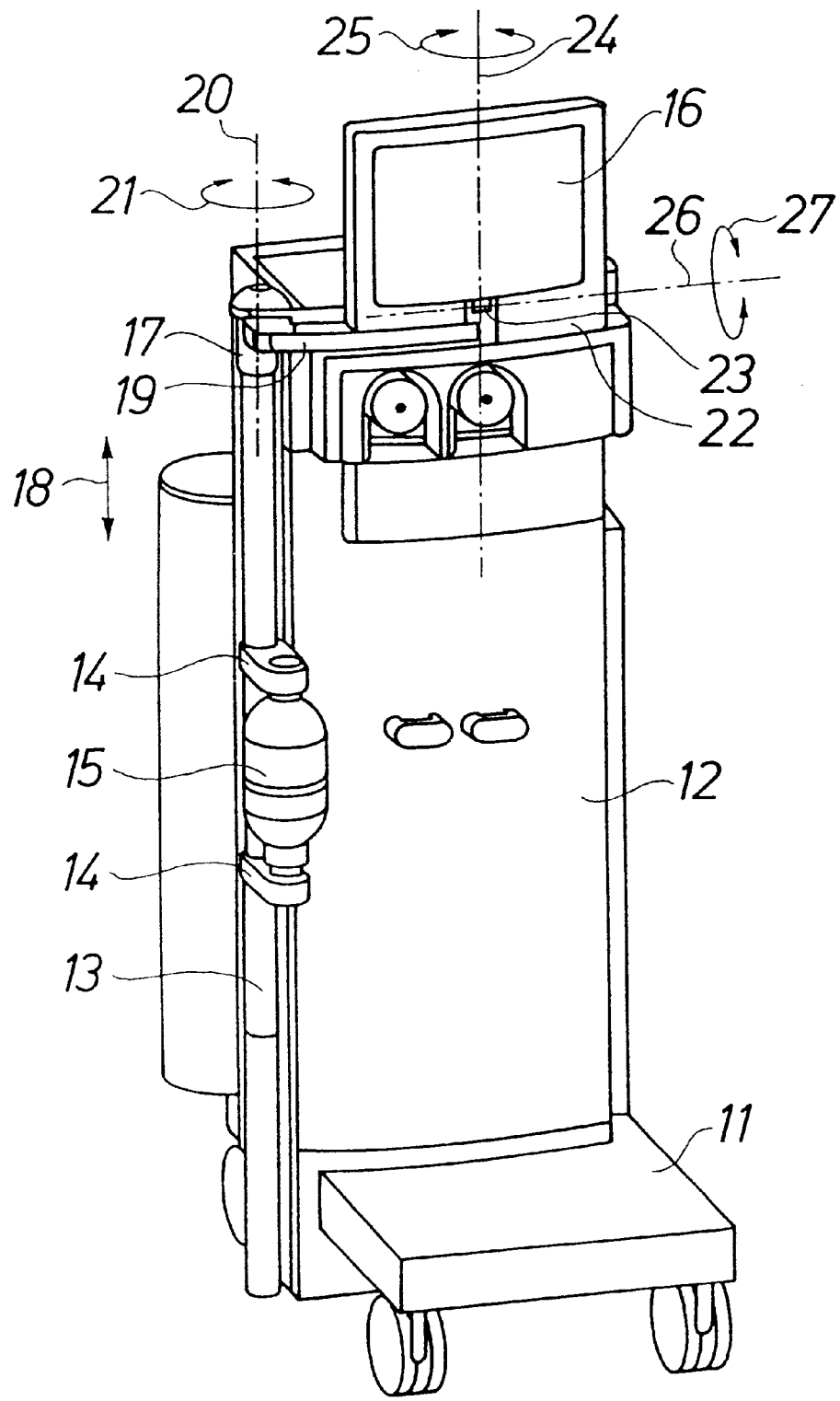
FIG. 1 is a perspective view of a dialysis machine according to the invention with the touch screen in a normal position in order that a person standing at the machine shall be able to comfortably control the same.

The dialysis machine comprises a mobile chassi 11 and it has at the front side 12 thereof common means for connecting the hoses by means of which the patient shall be connected to the dialysis machine. At the side of the machine a vertical cylindrical guide 13 is provided, and on this guide there are holders 14 for mounting a cartridge 15 containing powder which shall form an ingredient of the dialysis liquid. A flat touch screen 16 which shows several operational parameters and is provided with symbols and fields for adjustment of the dialysis machine by relevant symbols and fields, respectively, on the screen being touched can be adjusted vertically and can be universally pivoted on the dialysis machine and can be fixed in the desired adjusted position.

A bracket 17 is mounted for displacement on the guide 13. It can be displaced up and down on the guide as indicated by a double arrow 18 and can be locked in the desired displaced position by means of a lock mechanism such as a clamping device which is controlled by means of a knob, lever or another control element but preferably is controlled electrically by means of a servo motor. The bracket 17 forms a bearing for an arm 19 which can be rotated on the bracket about a vertical axis indicated by a dot-and-dash line 20. The possibility of rotating arm 19 about this axis is indicated by a double arrow 21. A lock mechanism can be provided on bracket 17 for locking arm 19 in the desired rotated position on bracket 17 but the same lock mechanism as used for locking bracket on guide 13 can be used for locking arm 19 in the desired rotated position. The lock mechanism in that case can be constructed in a similar way as that applied for example for shower holders.

The arm 19 carries at the outer free end thereof a holder 22 which at a joint 23 is connected with arm 19 for rotation about a vertical axis which is indicated with dot-and-dash line 24. The possibility to rotate holder 22 about this axis is indicated by a double arrow 25. A lock mechanism can be provided on arm 19 for locking holder 22 in the desired rotated position in relation to arm 19 in joint 13 but it is also possible for the holder to be freely rotated on arm 19. Holder 22 can also be rotated about a horizontal axis which is indicated by a dot-and-dash line 26. The possibility of rotation about this axis is indicated by a double arrow 27. The touch screen 16 is carried by holder 22 and thus can be adjusted to the desired rotated position and inclined position on arm 19. Preferably the joint 23 comprises a universal joint (ball joint) which allows adjustment of holder 22 and thus touch screen 16 about axis 24 as well as axis 26. There is a lock mechanism for arresting the touch screen in the desired inclined position by clamping the holder 22 in the joint 23. This lock mechanism can be of the same basic embodiment as the lock mechanism for holder 17 and arm 19, respectively.

It is suitable that the weight of the touch screen is counterbalanced by a counterweight so that the screen can be adjusted to different positions in a "weightless" condition. The counterbalancing can be effected by the holder 17 being connected to one end of a rope extending over a pulley at the top of the machine and at the other end of the rope being connected to a counterweight.

Figure 5:
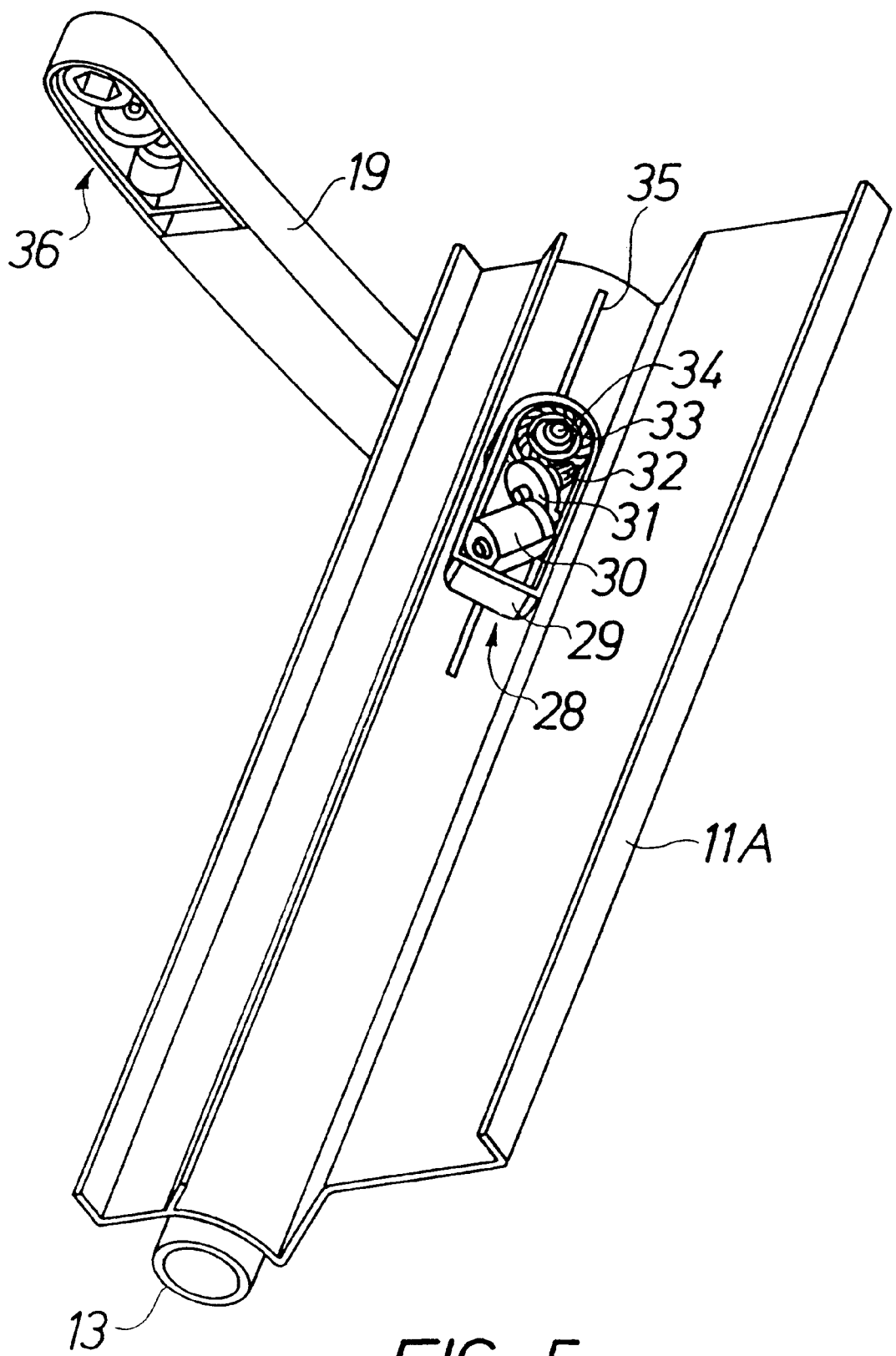
FIG. 5 is an enlarged fragmentary perspective view, portions being broken away, which discloses an embodiment of a lock mechanism with electric servo motor.

FIG. 5 discloses an embodiment of a lock mechanism with an electric servo motor. At the backside of an element 11A forming part of the chassi 11 a housing 29 with an electric servo motor 30 is provided. Via a gear mechanism 31 and a worm gear 32 the servo motor engages a nut 33 constructed as a worm wheel, on a screw 34. This screw can be displaced along guide 13 together with bracket 17 in a slot 35 and forms a clamp screw for a lock mechanism of a known type, which at jaws embraces guide 13. By the nut being sightened by means of the servo motor the jaws can be brought to clamp guide 13, and by the nut being loosened by means of the servo motor the jaws can be brought to release the guide. The housing 29 is guided for linear displacement on element 11A. A corresponding lock mechanism 36 is shown in arm 19 for holder 22. The servo controlled lock mechanisms can be easily controlled from the touch screen.

Normally, when the dialysis machine is to be controlled by a person standing on the floor in front of the machine the touch screen 16 is located in the manner shown in FIG. 1. In this position the touch screen is comfortably available to said person for reading of the parameters shown on the touch screen and for controlling the machine in the manner as required for a dialysis treatment to be made or pending by touching the relevant symbols or fields on the touch screen. When the touch screen is mounted in the manner proposed according to the invention and as described above the touch screen can, however, contrary to the situation in case of a machine having a fixedly mounted touch screen be adjusted vertically and possibly be inclined about axis 26 in order to be adjusted to the length of the operator. By these adjustments and also by adjustment about axes 20 and 24 the touch screen can be adapted to existing space conditions i.e. it can be adjusted so that the screen faces another direction than the machine. The position of the touch screen can also by adjusted as required in order to avoid incident light which makes reading of the screen more difficult.

Figure 2:
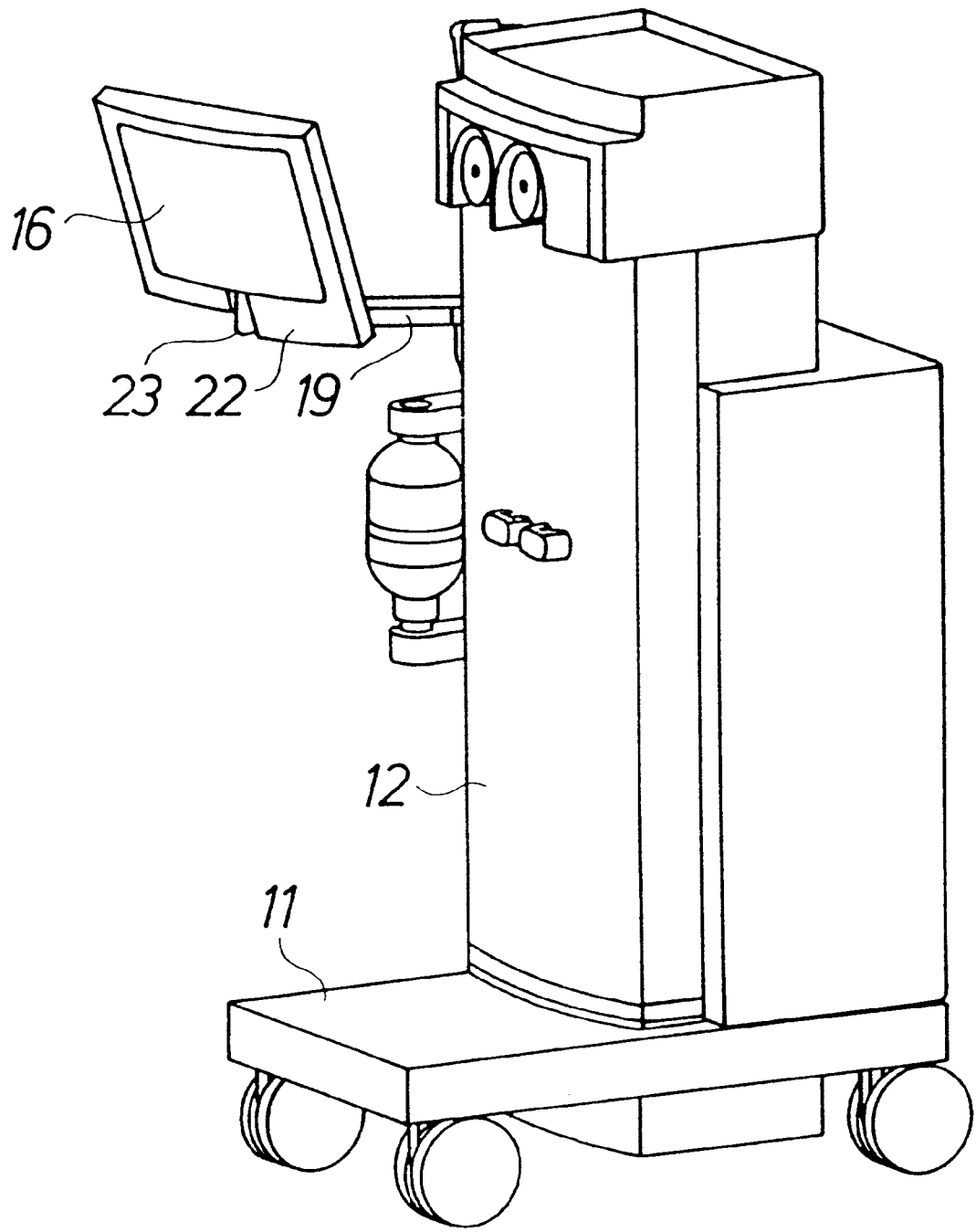
FIG. 2 is a corresponding perspective view with the touch screen adjusted to a position which is suitable in order that the control of the machine in self-care can be effected comfortably by a person sitting or laying adjacent the machine.

When the machine in self-care shall be controlled by the person who undergoes dialysis treatment and must be not in a standing but in a sitting or laying position the dialysis machine can be moved to the side of the treatment chair or treatment bunk and the touch screen 16 can be placed in the position which provides the best comfort to the patient thanks to the vertical adjustment and the universal movability. Then, the touch screen can be freely adjusted vertically to be adapted to different chair and bunk heights, and it can be rotated and inclined in order that the dialysis patient shall be able to read the screen at optimal comfort. Moreover, the touch screen can be temporarily adjusted to another position in order that it can be read by an external supervisor, e.g. a relation in the home or a chief physician at a central treatment place, for temporary check of the dialysis treatment without disturbance of the hose connection between the machine and the patient and without the necessity of moving the machine from the chair or bunk. In FIG. 2 the machine is shown in position for self-care wherein bracket 17 has been displaced downwards along guide 13 and arm 19 has been rotated outwards from the front side 12 and wherein bracket and arm have been arrested in this position. The touch screen 16 has been rotated to a suitable position on arm 19 about the axis indicated by the dot-and-dash line 24 (FIG. 1), and in FIG. 2 it is arrested in a forwardly inclined position on the axis 26 (FIG. 1) but can as well be arrested in a substantially vertical position. It is important that the position is such that the touch screen can be comfortably read and reached by the patient. There are practically no limitations regarding the adjustment of the touch screen when it is made universally adjustable in the manner described above.

Figure 3:
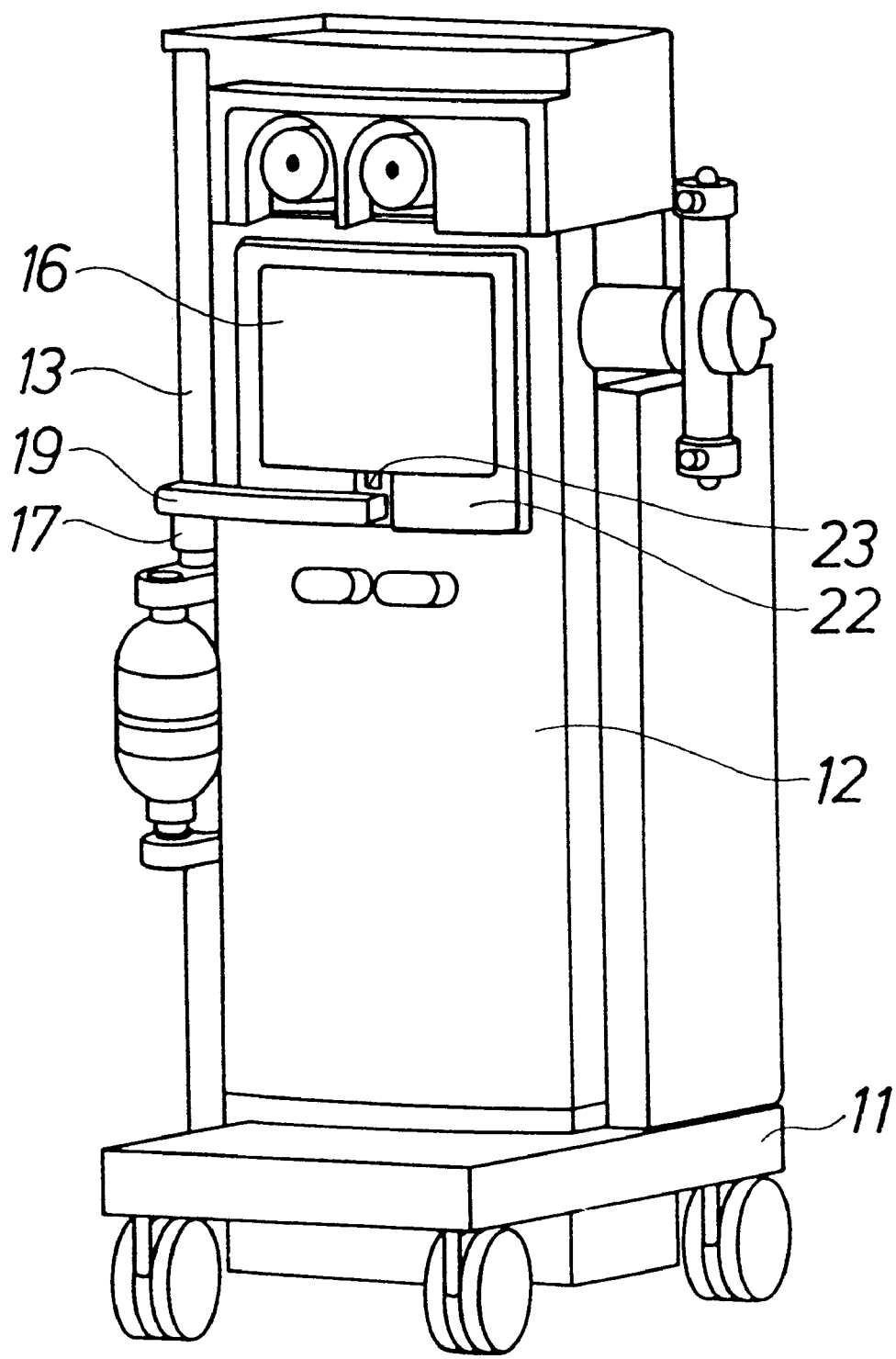
FIG. 3 is a corresponding perspective view with the touch screen in a storing or shipping position.

The touch screen can also in the machine according to the invention be adjusted to the position according to FIG. 3, i.e. below the uppermost part of the machine where pumps and connections are provided, which is an ideal position for transport of the machine within the hospital or home or when storing the machine because the machine with the touch screen in this position requires less space. The position of the touch screen shown in FIG. 3 is also advantageous from the point of view that service of the machine will be facilitated and the machine is smaller and cheaper to ship at delivery.

Figure 4:
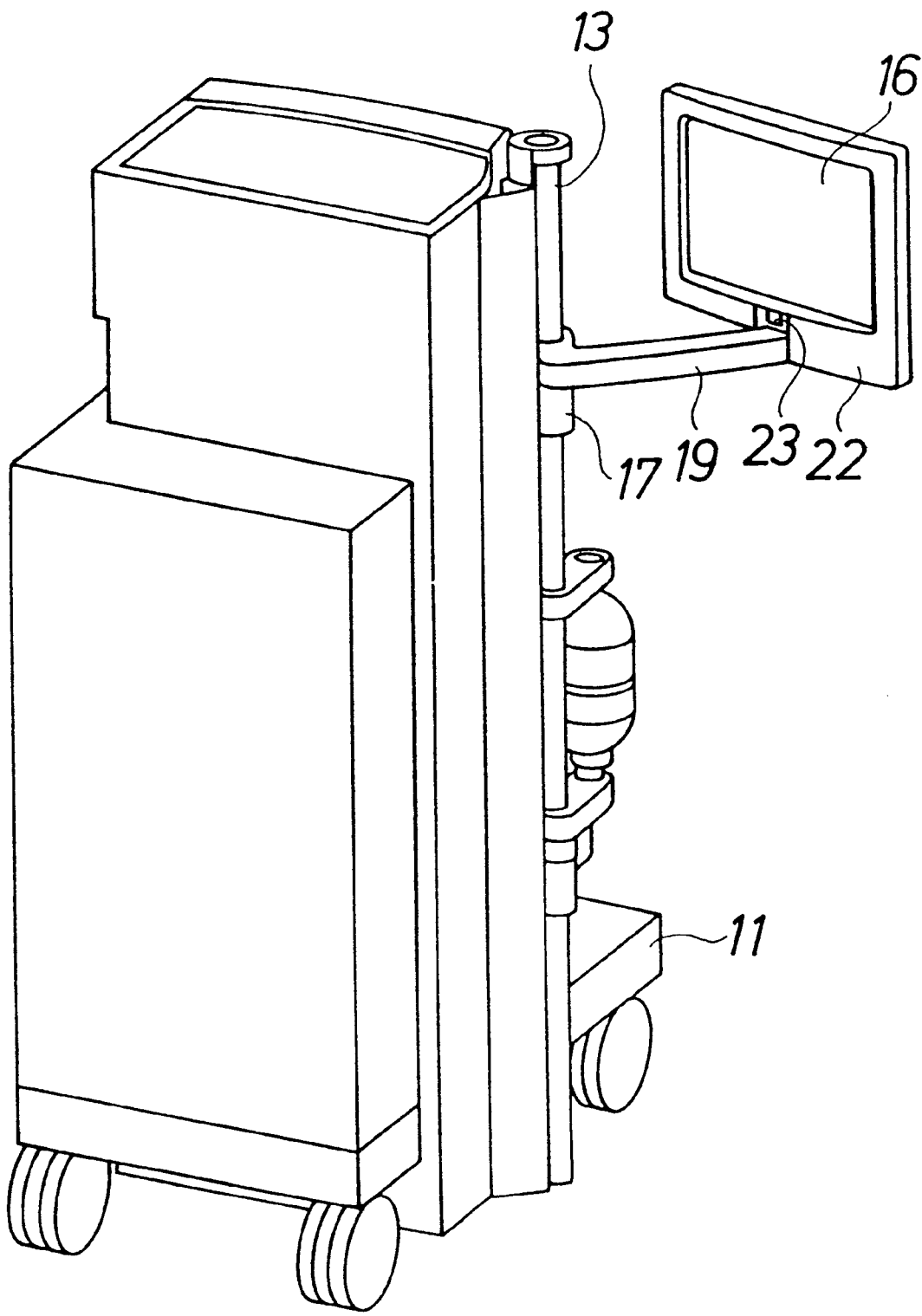
FIG. 4 is a corresponding perspective view with the touch screen in service position in which it can be seen from the backside of the machine.

When operations are to be made in the dialysis machine at the backside thereof the arrangement of the touch screen in the manner proposed according to the invention provides the further advantage that the touch screen can be adjusted to the position according to FIG. 4, which means that the touch screen is turned backwards so that the service technician can control the machine and can read the effect of operations made from the backside of the machine.

What is claimed is:

1. A dialysis machine for hospital care and self-care with a control panel provided as a touch screen, the dialysis machine comprising a chassis having connectors for connecting a patient to the machine and wherein the touch screen is coupled to the chassis so that it can be adjusted to different desired vertical and horizontal positions with respect to the chassis and can be locked in a desired vertical and horizontal position with respect to the chassis.

2. The dialysis machine according to claim 1 wherein the adjustable touch screen is supported by a bracket which can be displaced and on a vertical guide provided on the machine, and can be locked in a desired displaced position.

3. The dialysis machine according to claim 2 wherein the bracket can be rotated on the guide and can be locked in a desired rotated position.

4. The dialysis machine according to claim 3 wherein the touch screen is provided on a holder which is mounted for rotation about a first vertical axis and a horizontal axis at a free end of an arm carried on the bracket at an other end thereof for rotation about a second vertical axis.

5. The dialysis machine according to claim 4 wherein the means for locking the touch screen in the desired displaced position comprises an electricl servo device.

6. The dialysis machine according to claim 1 wherein the weight of the touch screen is counterbalanced.

7. A dialysis machine comprising:
   a chassis including at least one member for connecting at least one hose for allowing a patient to be connected to the dialysis machine; and
   a touch screen that is coupled to the chassis so as to be adjustable in a vertical and a horizontal direction with respect to the chassis and rotated about an axis parallel to a plane of the chassis.

8. The dialysis machine of claim 7 wherein the screen is coupled to the chassis by a vertical guide that allows the touch screen to move vertically with respect to the chassis.

9. The dialysis machine of claim 7 wherein the screen is coupled to an arm that can move vertically and horizontally with respect to the chassis.

10. The dialysis machine of claim 7 wherein the screen is received within a bracket that is coupled to an arm that allows the screen and bracket to rotate about an axis of the arm.

11. The dialysis machine of claim 7 including means for locking the screen in a specific orientation with respect to the chassis.

12. A dialysis machine comprising:
    a body member having a front face and at least one connection for allowing the connection of a patient to the dialysis machine;
    an arm coupled to the body that is moveable in a horizontal and vertical direction with respect to the front face; and
    a touch screen for controlling the dialysis machine that is coupled to the arm, the touch screen being rotatable about an axis of the arm.

13. The dialysis machine of claim 12 including a member for locking the arm in a position relative to the body member.

14. The dialysis machine of claim 12 including a member for locking the touch screen in a position relative to the arm.

15. The dialysis machine of claim 12 wherein the touch screen is secured to a bracket and the arm is connected to the bracket.

16. The dialysis machine of claim 12 including a vertical guide connected to the body and wherein the arm is connected to the vertical guide.

17. A dialysis machine comprising:
    a body including connections for allowing a patient to be coupled to the body member;
    an arm coupled to the body in such a manner as to allow the arm to move in a horizontal and vertical direction with respect to the body;
    a touch screen that is coupled to the arm in such a manner that the touch screen can move vertically and horizontally with respect to the body, the touch screen including means for controlling at least certain operations of the dialysis machine; and
    a locking member for locking the screen in a specific position with respect to the body.

18. The dialysis machine of claim 17 wherein the touch screen can rotate about an axis of the arm.

19. The dialysis member of claim 17 wherein the locking member locks the arm in a specific position.

20. A method for providing dialysis comprising:
    providing a dialysis machine having a body that includes connections for connecting a patient to the dialysis machine and a touch screen that controls functions of the dialysis machine; connecting the patent to the dialysis machine; and
    allowing the patient to adjust the touch screen along three separate axis with respect to the body.

21. The method of claim 20 including the steps of:
    allowing the patient to adjust the screen to a specific position; and
    locking the screen in the position.

* * * * *